United States Patent [19]

Katsoulis

[11] Patent Number: 5,486,566
[45] Date of Patent: Jan. 23, 1996

[54] SILOXANE GELS

[75] Inventor: Dimitris E. Katsoulis, Midland, Mich.

[73] Assignee: Dow Corning Corporation, Midland, Mich.

[21] Appl. No.: 311,246

[22] Filed: Sep. 23, 1994

[51] Int. Cl.[6] .............................. A61K 7/32; C08K 5/09; C08K 5/098
[52] U.S. Cl. .......................... 524/773; 524/777; 524/731; 524/860; 424/67; 424/65
[58] Field of Search ..................................... 524/777, 773, 524/860, 731; 424/67, 65

[56] References Cited

U.S. PATENT DOCUMENTS

| Re. 25,727 | 2/1965 | Haluska | 260/448.2 |
|---|---|---|---|
| 4,268,499 | 5/1981 | Keil | 424/68 |
| 4,781,917 | 11/1988 | Luebbe et al. | 424/65 |
| 4,980,156 | 12/1990 | Raleigh | 424/66 |
| 5,216,033 | 6/1993 | Pereiera et al. | 514/844 |
| 5,284,649 | 2/1994 | Juneja | 424/67 |
| 5,362,482 | 11/1994 | Yoneyama et al. | 424/69 |
| 5,401,870 | 3/1995 | Raleigh et al. | 556/445 |

FOREIGN PATENT DOCUMENTS

| WO9118587 | 12/1991 | WIPO . |
|---|---|---|
| WO9323008 | 11/1993 | WIPO . |

*Primary Examiner*—John C. Bleutge
*Assistant Examiner*—Margaret W. Glass
*Attorney, Agent, or Firm*—James DeCesare

[57] ABSTRACT

A gel suitable for use in various personal care applications is provided. The improved gel contains an amide-free gelator; a siloxane polyether for strengthening the gel, and increasing its firmness, rigidity, and adhesion to substrates; and a volatile methyl siloxane. Preferably, the gel includes 1 to 98.9 percent by weight of the siloxane polyether; 0.1 to 20 percent by weight of 12-hydroxystearic acid or metal salts of 12-hydroxystearic acid; and 1 to 98.9 percent by weight of a volatile methyl siloxane having a boiling point less than two hundred-fifty degrees Centigrade and a viscosity of 0.65 to about 5.0 centistoke ($mm^2/s$).

1 Claim, 1 Drawing Sheet

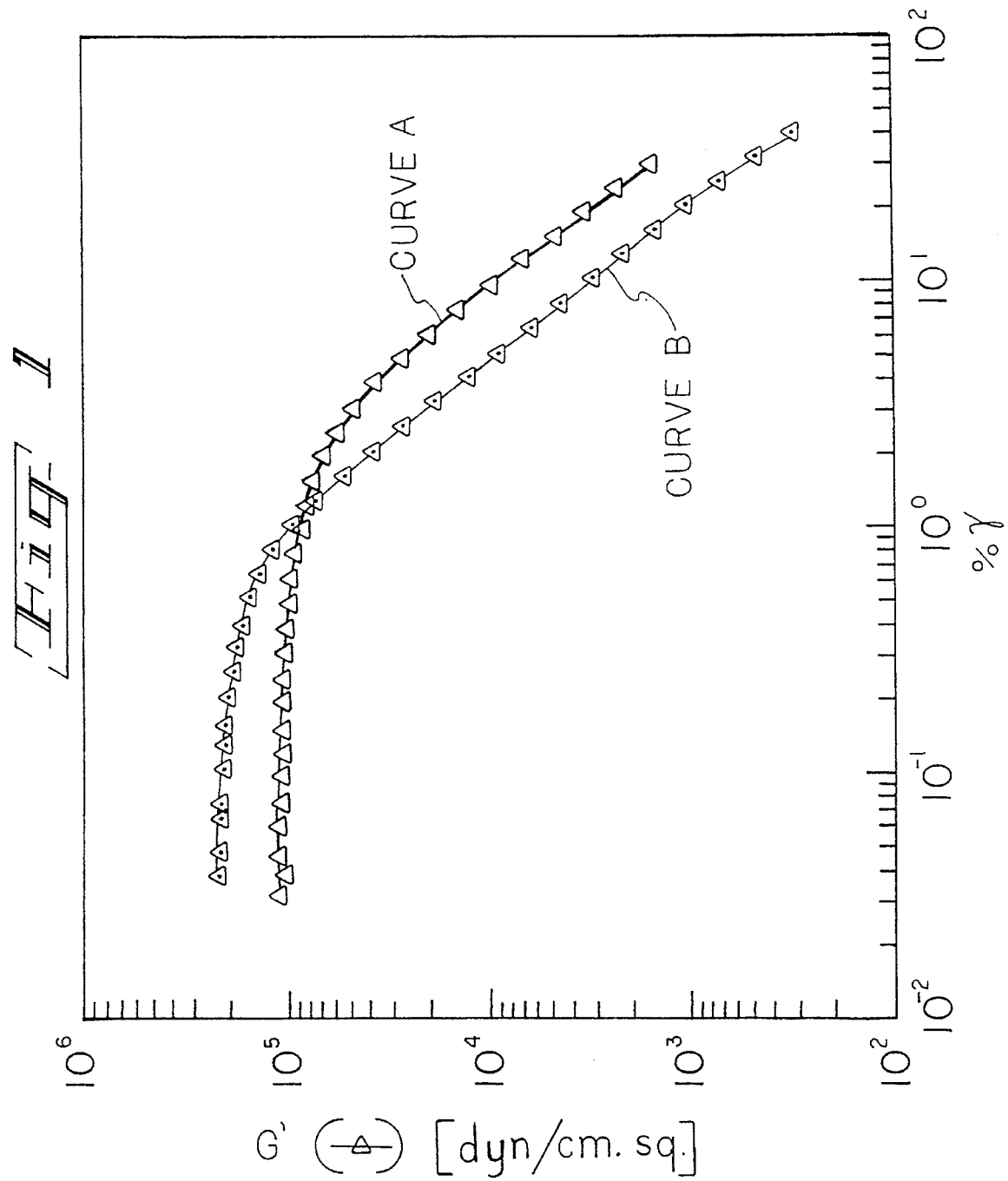

SILOXANE GELS

BACKGROUND OF THE INVENTION

This invention is directed to a clear firm gel suitable for use in various personal care applications. The improved gel includes an amide-free gelator; a siloxane polyether for strengthening the gel, and increasing its firmness, rigidity, and adhesion to substrates; and a methyl siloxane.

Recent trends in consumer buying has shifted in emphasis to a demand for clear products. These products range from fuels for automotive vehicles, to household and personal care products including dish washing and laundry detergents, as well as skin and hair care products in the form of lotions, solutions, and gels. One is apt to find on store shelves consumer oriented products such as clear shampoos, clear sunscreens, clear bath oils, clear deodorants, clear antiperspirants, and clear dentifrices. Since consumers tend to equate clarity with environmental friendliness and purity, the demand for clear products is likely to continue.

It is difficult to produce a clear product. In the case of stick type products, it is also difficult to produce a solid product with the appropriate rigidity. Not all basic ingredients necessary to formulate clear products lend themselves to clarity, or to firmness for that matter, particularly when they are combined with all of the other ingredients required for a successful formulated product. This is especially true in formulations found in the personal care arena.

Thus, the problem sought to be solved by the present invention is the production of a gel product, suitable for use as a base ingredient in personal care applications. This problem is solved according to the invention, by combining only "certain" basic components into a formulation which meet "certain" criteria.

The benefits and advantages derived from the invention are that a solid product which is effective for use as a component in personal care products can effectively be produced which will meet consumer demands for clarity and rigidity in the marketplace.

SUMMARY OF THE INVENTION

The invention relates to a gel containing 1 to 98.9 percent by weight of a siloxane polyether; 0.1 to 20 percent by weight of an amide-free gelator which can be 12-hydroxystearic acid or the metal salts of 12-hydroxystearic acid; and 1 to 98.9 percent by weight of a volatile methyl siloxane. The volatile methyl siloxane has a boiling point less than two hundred-fifty degrees Centigrade and a viscosity of 0.65 to about 5.0 centistoke (mm$^2$/s).

While not being bound by any particular theory, it is believed that the increase of strength of the gels of the invention, as well as their increase in clarity and adhesion to substrates, is due to an increased interaction between the 12-hydroxystearic acid gelator and the siloxane polyether. Because the gelator is amide-free, this interaction is unhindered by the presence of any amide-type co-gelator, such as those taught in U.S. Pat. No. 0530671/EP 0 531 337 which was published Nov. 5, 1993 as WO 93/23008.

In that WO 93/23008 publication, a use is suggested of certain long-chain alkyl modified polysiloxane-polyoxyalkylene copolymers having a structure corresponding to what is described as $MD_xD'_yD''_zM$, by way of reference to an EPO Application 0373424/U.S. Pat. No. 4,980,156.

In comparison, the siloxane polyethers of the present invention have a structure of only $MD''_zM$, indicating a significantly different molecule, with a significantly different structure, and obviously significantly different properties. In addition, the siloxane polyethers of the present invention differ from the molecules described in the EPO Application 0373424/U.S. Pat. No. 4,980,156, in that the EPO Application 0373424/U.S. Pat. No. 4,980,156 does not suggest the use of a $MD''_zM$ type siloxane polyether with an oxyalkylene segment consisting of only oxypropylene units $-(C_3H_6O)_s-$. In an alternate embodiment, siloxane polyethers of the type $QD_zQ$ are employed, where Q is the oxyalkylene segment including the linking group, and this type of molecule is also not suggested by EPO Application 0373424/U.S. Pat. No. 4980156.

Thus, according to the present invention, the siloxane polyethers function to increase the intermolecular forces between the volatile methyl siloxane and the 12-hydroxystearic acid gelator, in order to control the size and the number of the microfibers which are formed, and this in turn improves the strength and the clarity of the gels.

Furthermore, the siloxane polyethers of this invention function to increase the solubility of the amide-free 12-hydroxystearic acid gelator in the volatile methyl siloxane. As a result, a large number of nucleation sites are formed during crystallization, and these sites have the potential of producing a large number of microfibers. A high fiber density is thereby produced, and the high fiber density causes the gels to become stronger in exhibiting a higher modulus. Since the microfibers are of a very small size, they cause less light scattering and the gels are transparent.

These and other features, objects, and advantages, of the present invention will become more apparent from a consideration of the following detailed description thereof, wherein reference is made to the single FIG. 1 in the drawing.

BRIEF DESCRIPTION OF THE DRAWING

The single FIG. 1 in the drawing is a graphical representation of strain sweep curves measured at 5 radians per second (48 revolutions per minute) for two gels which were prepared in accordance with Example 7. Curve A in the drawing figure represents Gel (A) prepared according to Example 7, while Curve B in the drawing FIGURE represents Gel (B) prepared according to Example 7. Gel (B) represents the present invention, while Gel (A) does not represent the invention.

The drawing FIGURE shows that the storage modulus G' of Gel (B) is higher than the storage modulus G' of Gel (A). This indicates that the consistency of Gel (B) is firmer than the consistency of Gel (A).

Thus, the siloxane polyether used to prepare Gel (B) of the invention functions to increase the compatibility of the 12-hydroxystearic acid gelator with the volatile methyl siloxane when hot. Upon cooling, a large number of nucleation sites are thereby formed, which create a high density of microfibers and thus a firmer Gel (B); in comparison to Gel (A) which did not contain the siloxane polyether according to the invention.

DETAILED DESCRIPTION OF THE INVENTION

Gels according to the invention contain 1 to 98.9 percent by weight of a siloxane polyether; 0.1 to 20 percent by weight of an amide-free gelator; and 1 to 98.9 percent by weight of a volatile methyl siloxane. Preferably, the gels contain 1 to 10 percent by weight of the siloxane polyether; 0.1 to 4 percent by weight of the amide-free gelator; and 1 to 90 percent by weight of the volatile methyl siloxane.

The siloxane polyether of the present invention is a compound having one of the following formulas:

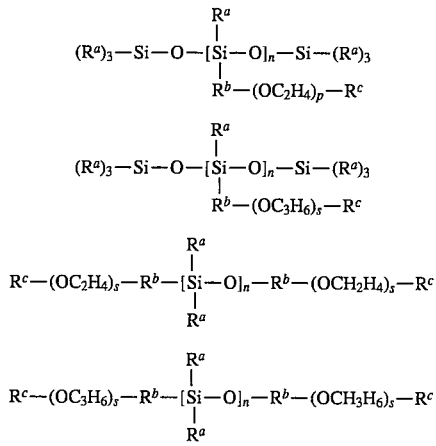

wherein $R^a$ is an alkyl group of one to six carbon atoms; $R^b$ is the linking group $—C_mH_{2m}—$; $R^c$ is a terminating radical which can be hydroxyl or alkoxy such as methoxy, ethoxy, and propoxy; m has a value of two to eight; p and s each have values between one and thirty; and n has a value of one to forty.

Methods of making such siloxane polyether compounds are known in the art, and are described in detail for example, in the volume "Chemistry and Technology of Silicones", Walter Noll, Academic Press Inc., 1968, Pages 373–376.

The oxyalkylene segment of the siloxane polyether consists of only oxyethylene units $—(C_2H_4O)_p—$ or only oxypropylene units $—(C_3H_6O)_s—$, but the oxypropylene unit $—(C_3H_6O)_s—$ is the most preferred oxyalkylene segment for purposes of the present invention.

The amide-free gelator is 12-hydroxystearic acid or a metal salt of 12-hydroxystearic acid. The acid has the formula $CH_3(CH_2)_5CH(OH)(CH_2)_{10}COOH$. Metal salts of 12-hydroxystearic acid can also be employed as gelator. Such salts have the formula $[C_6H_{13}—CH(OH)—(CH_2)_{10}—COO]_nM$ in which M indicates a metal such as Li+, Na+, K+, Rb+, Cs+, Mg(2+), Ca(2+), Sr(2+), Ba(2+), Mn(2+), Ni(2+), Cu(2+), Zn(2+), Cd(2+), Hg(2+), Co(2+) and Pb(2+); and the value of n is one for monovalent cations and two for divalent cations. An example of metal salts suitable for use according to the invention are calcium 12-hydroxystearate and lithium 12-hydroxystearate. These metal salts can be prepared by the direct neutralization of 12-hydroxystearic acid with a metal base such as sodium hydroxide or potassium hydroxide. The metal salts can also be prepared by a metathesis reaction of a simple metal salt such as sodium 12-hydroxystearate with a metal sulfate salt or a metal chloride salt such as zinc chloride or copper sulfate.

The third component is a volatile methyl siloxane, which is a low viscosity silicone fluid which corresponds to the average unit formula $(CH_3)_aSiO_{(4-a)/2}$ in which a has an average value of two or three. The fluid contains siloxane units joined by Si—O—Si bonds. Representative units present in the fluid molecule are the monofunctional unit $(CH_3)_3SiO_{1/2}$ and the difunctional unit $(CH_3)_2SiO_{2/2}$. The presence of the trifunctional unit $CH_3SiO_{3/2}$ will generally result in the formation of branched cyclic volatile methyl siloxanes. The presence of the tetrafunctional unit $SiO_{4/2}$ will generally result in the formation of branched linear volatile methyl siloxanes. These units are present in molar amounts such that there is provided an average of from about two to three methyl groups per silicon atom in the fluid.

These fluids generally have a viscosity of less than ten centistoke (mm²/s). Representative volatile methyl siloxanes are cyclopolysiloxanes of the formula $[(CH_3)_2SiO]_x$, and linear siloxanes of the formula $(CH_3)_3SiO[(CH_3)_2SiO]_ySi(CH_3)_3$, in which x has a value of three to six, and y has a value of zero to five. These volatile methyl siloxanes have boiling points generally less than two hundred-fifty degrees Centigrade, and the viscosity is typically from about 0.65 to about 5.0 centistoke (mm²/s).

Some structures which are representative of volatile methyl siloxanes are shown below:

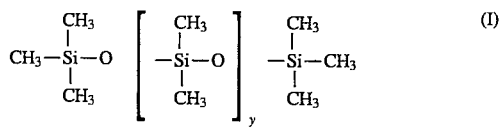

(I)

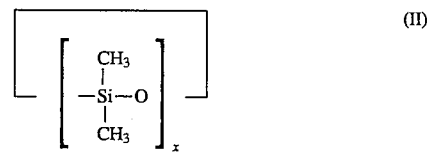

(II)

(III)

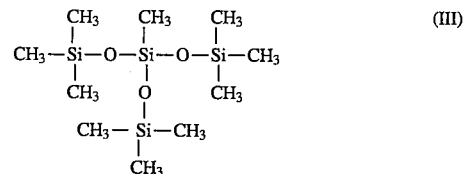

(IV)

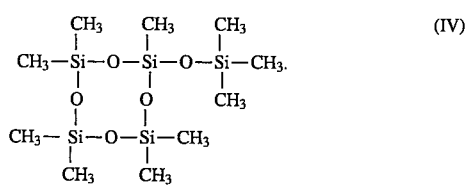

Structure I represents a linear volatile methyl siloxane. Structure II represents a cyclic volatile methyl siloxane. Structure III represents a branched linear volatile methyl siloxane. Structure IV represents a branched cyclic volatile methyl siloxane. The values of x and y in Structures I and II are the same as noted previously. The cyclic volatile methyl siloxane (II) has been assigned the International Nomenclature Cosmetic Ingredient (INCI) name "CYCLOMETHICONE" by *The Cosmetics, Toiletries and Fragrance Association, Inc.* (CTFA), Washington, D.C.

The cyclic and linear methyl siloxanes are clear fluids, and are essentially odorless, nontoxic, non-greasy and non-stinging. Cosmetically, the fluids are nonirritating to skin, spread easily when applied to the skin, and once applied, evaporate leaving behind no residue.

The volatile methyl siloxanes leave substantially no residue after thirty minutes at room temperature when one gram of the fluid is placed at the center of No. 1 circular filter paper which has a diameter of 185 millimeters and which is supported at its perimeter in open room atmosphere.

Some representative linear volatile methyl siloxanes are hexamethyldisiloxane which has a boiling point of 100 degrees Centigrade and the formula $Me_3SiOSiMe_3$; octamethyltrisiloxane which has a boiling point of 152 degrees Centigrade and the formula $Me_3SiOMe_2SiOSiMe_3$; decamethyltetrasiloxane which has a boiling point of 194 degrees Centigrade and the formula $Me_3SiO(Me_2SiO)_2SiMe_3$;

dodecamethylpentasiloxane which has a boiling point of 229 degrees Centigrade and the formula $Me_3SiO(Me_2SiO)_3SiMe_3$; tetradecamethylhexasiloxane which has a boiling point of 184 degrees Centigrade and the formula $Me_3SiO(Me_2SiO)_4SiMe_3$; and hexadecamethylheptasiloxane which has a boiling point of 184 degrees Centigrade and the formula $Me_3SiO(Me_2SiO)_5SiMe_3$.

Some representative cyclic volatile methyl siloxanes are hexamethylcyclotrisiloxane which has a boiling point of 133 degrees Centigrade and the formula $[(Me_2)SiO]_3$; octamethylcyclotetrasiloxane which has a boiling point of 171 degrees Centigrade and the formula $[(Me_2)SiO]_4$; decamethylcyclopentasiloxane which has a boiling point of 205 degrees Centigrade and the formula $[(Me_2)SiO]_5$; and dodecamethylcyclohexasiloxane which has a boiling point of 245 degrees Centigrade and the formula $[(Me_2)SiO]_6$.

Generally, the volatile methyl siloxanes may be used alone, or mixed together. Mixtures of the fluids will result in a volatile material having an evaporating behavior different from any one of the individual fluids.

A petition to the EPA filed in late 1992 is pending seeking exemption of these volatile methyl siloxanes (VMS) from regulation as a VOC. The basis for the petition is that the volatile methyl siloxanes do not contribute to, and in some cases actually inhibit the formation of tropospheric ozone. Thus, the volatile methyl siloxanes have a lower ozone formation potential than ethane, which is the most reactive compound on a list of "exempt" VOC.

Furthermore, these volatile methyl siloxanes (VMS) have an atmospheric lifetime of between 10 to 30 days. Consequently, VMS compounds do not contribute significantly to global warming. Volatile methyl siloxanes have no potential to deplete stratospheric ozone due to their short atmospheric lifetimes so that they will not rise and accumulate in the stratosphere. VMS compounds also contain no chlorine or bromine atoms.

Volatile methyl siloxane compounds (VMS) neither attack the ozone layer nor do they contribute to tropospheric ozone formation (Smog), and they have minimum GLOBAL WARMING potential. Volatile methyl siloxane compounds are hence unique in possessing these three attributes simultaneously.

These volatile methyl siloxanes provide a viable solution to the problem of finding a suitable replacement for "outlawed" chemicals heretofore commonly used as components in personal care products.

The procedure for making the clear, firm, gel according to the invention is simply a matter of combining and mixing together three components. The mixture is heated to dissolve the gelator. The gel is formed when the mixture is cooled or allowed to cool.

The invention will be illustrated in more detail in the following examples.

EXAMPLE 1

In a one ounce glass vial, 3.1 grams of a mixture containing about 75 percent by weight of decamethylcyclopentasiloxane and about 25 percent by weight of dodecamethylcyclohexasiloxane, hereinafter referred to as "VMS" (volatile methyl siloxane), was mixed with one gram of a siloxane polyether having the formula $Me_3SiO$—[MeSi—$(CH_2)_3O$—$(CH_2CHCH_3O)_2OMe$]—$OSiMe_3$. This particular siloxane polyether is referred to hereinafter as siloxane polyether (I). To the resulting clear solution, 0.2 grams of 12-hydroxystearic acid were added, and the mixture was heated mildly on a hot plate. The 12-hydroxystearic acid dissolved before reaching its melting temperature of 80°–81° C. The clear solution was removed from the hot plate. Upon cooling and before reaching ambient temperature, a firm opaque gel was formed. The gelation rate was noted to be rapid. The gel was reheated and converted back to a clear solution. Upon cooling, a stiff opaque gel was again formed. Ten additional grams of the VMS were added to the gel, and the mixture was heated. Upon cooling, a translucent gel was obtained. The concentration of 12-hydroxystearic acid in the gel was 1.4 weight percent. At this low concentration, the gel was still stiff enough, that it would not brake down by either vigorous vortexing on a Thermolyne Maxi Mix II mixer, nor by vigorous shaking by hand.

EXAMPLE 2

Another gel was prepared in a manner analogous to that described in Example 1, by mixing together twenty grams of VMS, 0.88 grams of the siloxane polyether (I), and 0.2 grams of 12-hydroxystearic acid. The mixture was heated and a clear solution was obtained. Upon cooling, an opaque firm gel was formed. Vigorous vortexing did not disrupt the gel. One gram of absolute ethanol was added to the formulation, and by applying a slight amount of heat, the gel was converted to a clear solution. Upon cooling and upon the elapse of two hours, only a small portion of the solution had formed traces of a weak gel. Most of the mixture remained in liquid form, with some cloudy specs believed to be precipitated 12-hydroxystearic acid, which were clearly visible. This indicated that the gelator was very soluble in an alcohol, the presence of which prevents the gelation process.

EXAMPLE 3

Another gel was prepared by combining ten grams of VMS, one gram of the siloxane polyether (I) that contained about fifty weight percent of unreacted propylene oxide, and 0.2 grams of 12-hydroxystearic acid. The method described in Example 1 was again followed. The gel was opaque and firm, and did not brake down by vortexing. An amount of 0.44 grams of absolute ethanol was added to the gel, and upon heating and vortexing, an opaque liquid was obtained. When cooled, the mixture again gelled. This gel was breakable with vortexing, but it reformed within an hour by standing at room temperature.

EXAMPLE 4

The following gel formulation was prepared according to the method of Example 1, by mixing together eighty-eight weight percent of VMS, ten weight percent of the siloxane polyether (I), and two weight percent of 12-hydroxystearic acid. The resulting gel was firm and translucent. The gel was not disrupted by vortexing, shaking by hand, or by a Brinkman mechanical shaker set at maximum.

EXAMPLE 5

Six (6) gels analogous to the gel of Example 4 were prepared using the siloxane polyethers shown below. In the formulas, "Me" indicates the methyl group —$CH_3$. The gel formed with siloxane polyether (I) is described in the previous Example 4.

Polyether Formula (A) MDDM  $Me_3SiO$ $(Me_2SiO)_{103}(MeQSiO)_{9.5}$—$SiMe_3$ in which Q is —$(CH_2)_3(OCH_2CH_2)_{18}(OCH_2CHCH_3)_{18}OCOCH_3$ (B) MDDM $Me_3SiO(Me_2SiO)_{8.6}(MeQSiO)_{3.6}SiMe_3$ in which Q is —$(CH_2)_3(OCH_2CH_2)_{12}OH$ (I) MDM $Me_3SiO$—[$MeSi$—$(CH_2)_3O$—$(CH_2CHMeO)_2OMe$]—$OSiMe_3$ (II) QDQ HO—$(CH_2CH_2O)_{12}$ $(Me_2SiO)_{13}$—$(CH_2CH_2O)_{12}$—OH (III) MDM $Me_3SiO$—[$MeSi$—$(CH_2)_3O$—$(CH_2CH_2O)_7OH$]—$OSiMe_3$ (IV) MDM $Me_3SiO$—[$MeSi$—$(CH_2)_3O$—$(CH_2CH_2O)_{12}OH$]—$OSiMe_3$ The formulations for each of the gels was heated to dissolve the gelator. All of the mixtures formed hazy solutions. Gels were formed on cooling.

EXAMPLE 5A.

Another formulation containing 89.5 weight percent of VMS, ten weight percent of the siloxane polyether (I), and 0.5 weight percent of 12-hydroxystearic acid, formed a translucent gel. This gel could be disrupted by shaking for a few seconds with a Brinkman shaker set at 100.

EXAMPLE 6—Comparison

Two gels analogous to the gel made according to the procedure of Example 4, were prepared using siloxane polyethers (A) and (B). The formulas for these two siloxane polyethers are set forth above in Example 5. Siloxane polyethers (A) and (B) are of the type MDDM, in comparison to the siloxane polyethers (I) to (IV) of the invention, which correspond to types MDM and QDQ, as shown above in Example 5. Cloudy mixtures containing the siloxane polyethers (A) and (B) were heated on a hot plate at a temperature in excess of 80° C. Gel (B) which was formed with siloxane polyether (B), phase separated and required mixing prior to reaching the gel point, in order to obtain a "uniform-like" gel. Gels (A) and (B) were each shaken on a Brinkman wrist shaker operating at maximum speed. Gel (B) broke down first. Gel (A) was more resistant to breakage, although it began thinning after a time. Upon standing for one hour at ambient temperature, gels (A) and (B) were partially reformed, although gel (A) broke down again upon inversion of the vial, and gel (B) was noted to contain some non-gelled fluid.

EXAMPLE 7—Comparison

Two gels were prepared according to the method described in Example 1. Gel (A) contained 9.8 grams of the VMS and 0.2 grams of 12-hydroxystearic acid. Gel (A) did not contain a siloxane polyether and is not according to the invention. Gel (B) contained 15.2 grams of the VMS, 4.4 grams of siloxane polyether (I), and 0.4 grams of the gelator 12-hydroxystearic acid. Gel (B) is according to the invention. The mixture used to prepare gel (B) was clear when the solution was hot. The solution used to prepare gel (A) on the other hand, contained visible droplets of melted 12-hydroxystearic acid when it was heated. The hot solutions were each cast in a round stainless steel mold used on Rheometrics Inc. rheometers for measuring the strength of gels. Gels were formed on cooling. Gel (B) was less hazy than gel (A). Gel (B) was found to adhere to a greater extent on metal and Teflon substrates than gel (A).

Strain sweep curves were determined for each of the gels (A) and gel (B). These strain sweep curves at five rad/s are shown in the single FIGURE in the drawing. In the single FIGURE in the drawing, it will be noted that the storage modulus G' of gel (B) is higher than that of gel (A). This indicates that the consistency of gel (B) is firmer than that of gel (A). This improvement is believed to be due to the fact that the siloxane polyethers of the types MDM and QDQ increase the compatibility of the gelator with the VMS when the solution is hot. Because of this, upon cooling, a large number of nucleation sites are formed, and this creates a high density of microfibers and a firmer gel.

EXAMPLE 7A—Comparison

Another gel was prepared by mixing four weight percent of 12-hydroxystearic acid and 96 weight percent of the VMS. Again, no siloxane polyether was used to prepare the gel. Upon shaking, this comparison gel broke down easily.

EXAMPLE 8

Five (5) gels were prepared by combining the VMS, the siloxane polyether (I), and the 12-hydroxystearic acid gelator, according to the method described in Example 1. The amounts of the three ingredients used to prepare these five gels are shown below in Table I.

TABLE I

| Gel | wt. % VMS | wt. % (I) | wt. % 12-OH stearic acid | Comments |
| --- | --- | --- | --- | --- |
| A | 79 | 20 | 1 | weak gel |
| B | 84 | 15 | 1 | firmer than A |
| C | 89 | 10 | 1 | complete gel |
| D | 88.5 | 10 | 1.5 | gelled |
| E | 88.25 | 10 | 1.75 | gelled |

While gels (D) and (E) could be mechanically disrupted, they reformed on standing for about one day.

The foregoing examples illustrate that better gels can be obtained using the siloxane polyethers of the invention which are MDM and QDQ type ethers, in comparison to the longer chain ethers of the prior art such as the ethers of the types MDDM or MDDDM.

Other variations and modifications may be made in the compounds, compositions, and methods described herein, without departing from the essential features and concepts of the present invention.

The forms of the invention described herein are exemplary only, and are not intended as limitations on the scope of the invention as defined in the appended claims.

That which is claimed is:

1. A gel consisting essentially of (A) 1–98.9% by weight of the gel of a siloxane polyether with the formula

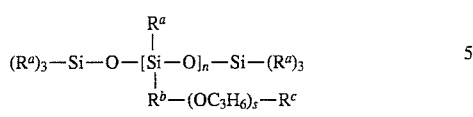

where $R^a$ is an alkyl group of 1–6 carbon atoms; $R^b$ is linking group —$C_mH_{2m}$—; $R^c$ is hydroxyl or alkoxy; m is 2–8; s is 1–30; and n is 1–40;

(B) 0.1–20% by weight of the gel of an amide-free gelator selected from the group consisting of 12-hydroxystearic acid and its metal salts; and (C) 1–98.9% by weight of the gel of a volatile methyl siloxane with a boiling point less than 250° C., a viscosity of 0.65–5 centistokes, and a formula selected from the group consisting of

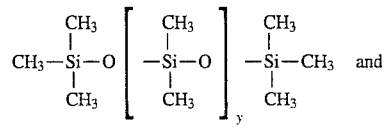

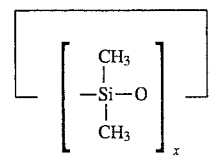

where x is 3–6 and y is 0–5.

* * * * *